US012016584B2

(12) United States Patent
Roche et al.

(10) Patent No.: US 12,016,584 B2
(45) Date of Patent: Jun. 25, 2024

(54) END EFFECTOR FOR A SURGICAL ARM

(71) Applicant: Zimmer Biomet Spine, Inc., Westminster, CO (US)

(72) Inventors: Nicolas Roche, Saint Medard en Jalles (FR); Nicolas Bidegaimberry, Gradignan (FR); David Rigotto, Saint Selve (FR)

(73) Assignee: Zimmer Biomet Spine, Inc., Westminster, CO (US)

( * ) Notice: Subject to any disclaimer, the term of this patent is extended or adjusted under 35 U.S.C. 154(b) by 504 days.

(21) Appl. No.: 17/196,637

(22) Filed: Mar. 9, 2021

(65) Prior Publication Data
US 2021/0282794 A1 Sep. 16, 2021

Related U.S. Application Data

(60) Provisional application No. 62/990,275, filed on Mar. 16, 2020.

(51) Int. Cl.
*A61B 17/29* (2006.01)
*A61B 17/28* (2006.01)
*A61B 90/50* (2016.01)

(52) U.S. Cl.
CPC .............. *A61B 17/29* (2013.01); *A61B 90/50* (2016.02); *A61B 2017/2845* (2013.01); *A61B 2017/2944* (2013.01); *A61B 2017/2946* (2013.01)

(58) Field of Classification Search
CPC ......... A61B 17/29; A61B 34/30; A61B 34/70; A61B 90/50; A61B 2017/00477; A61B 2017/2845; A61B 2017/2944; A61B 2017/2946; A61B 2034/302; A61B 2034/305; A61B 2034/301; A61B 2090/034
See application file for complete search history.

(56) References Cited

U.S. PATENT DOCUMENTS

| | | | |
|---|---|---|---|
| 4,473,249 A * | 9/1984 | Valentine | ............. B25J 15/0206 414/753.1 |
| 5,250,056 A * | 10/1993 | Hasson | .............. A61B 17/2909 606/208 |
| 6,860,877 B1 | 3/2005 | Sanchez et al. | |

(Continued)

FOREIGN PATENT DOCUMENTS

EP 0908139 4/1999

OTHER PUBLICATIONS

Notice of Allowance for Canada Patent Application No. 3,111,736, dated Apr. 13, 2023 1 pages.

(Continued)

*Primary Examiner* — Jocelin C Tanner
(74) *Attorney, Agent, or Firm* — Sheridan Ross P.C.

(57) ABSTRACT

An end effector for a surgical arm can include a housing, a stem secured to the housing configured to releasably couple the end effector to the surgical arm, a pair of opposing jaws pivotably coupled to the housing, a driving body translatable within the housing operable to open the opposing jaws and to close the opposing jaws, a drive spring, and a lock body movable between a locked position and an unlocked position, the locking body configured to engage the housing and the driving body in the locked position to limit distal translation of the driving body with respect to the housing.

22 Claims, 9 Drawing Sheets

(56) References Cited

U.S. PATENT DOCUMENTS

| | | |
|---|---|---|
| 8,764,769 B1* | 7/2014 | Rodriguez-Navarro ................... A61B 17/29 600/114 |
| 2008/0214925 A1 | 9/2008 | Wilson et al. |
| 2010/0185232 A1* | 7/2010 | Hughett, Sr. ...... A61B 18/1445 606/205 |
| 2019/0125354 A1 | 5/2019 | Deck et al. |

OTHER PUBLICATIONS

Official Action for Canada Patent Application No. 3,111,736, dated May 24, 2022 4 pages.
Extended Search Report for European Patent Application No. 21162994.4, dated Aug. 4, 2021 6 pages.

* cited by examiner

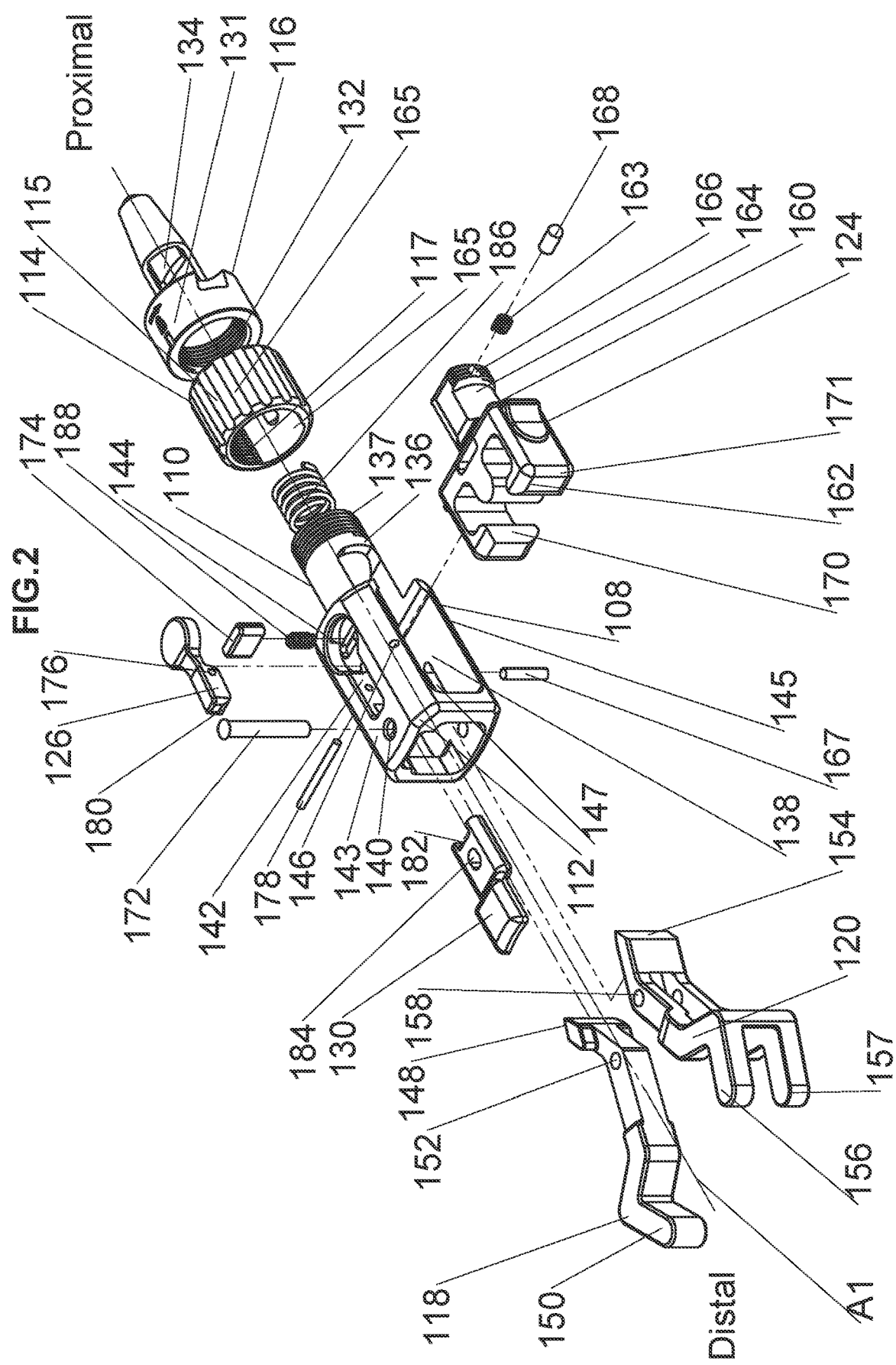

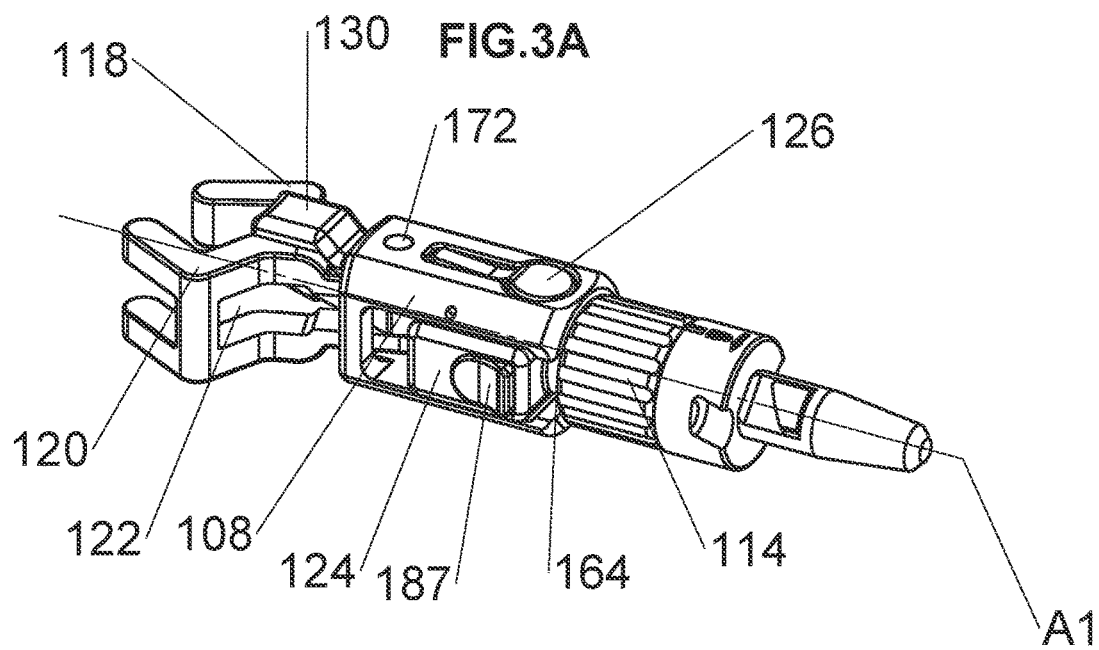
Distal  Proximal
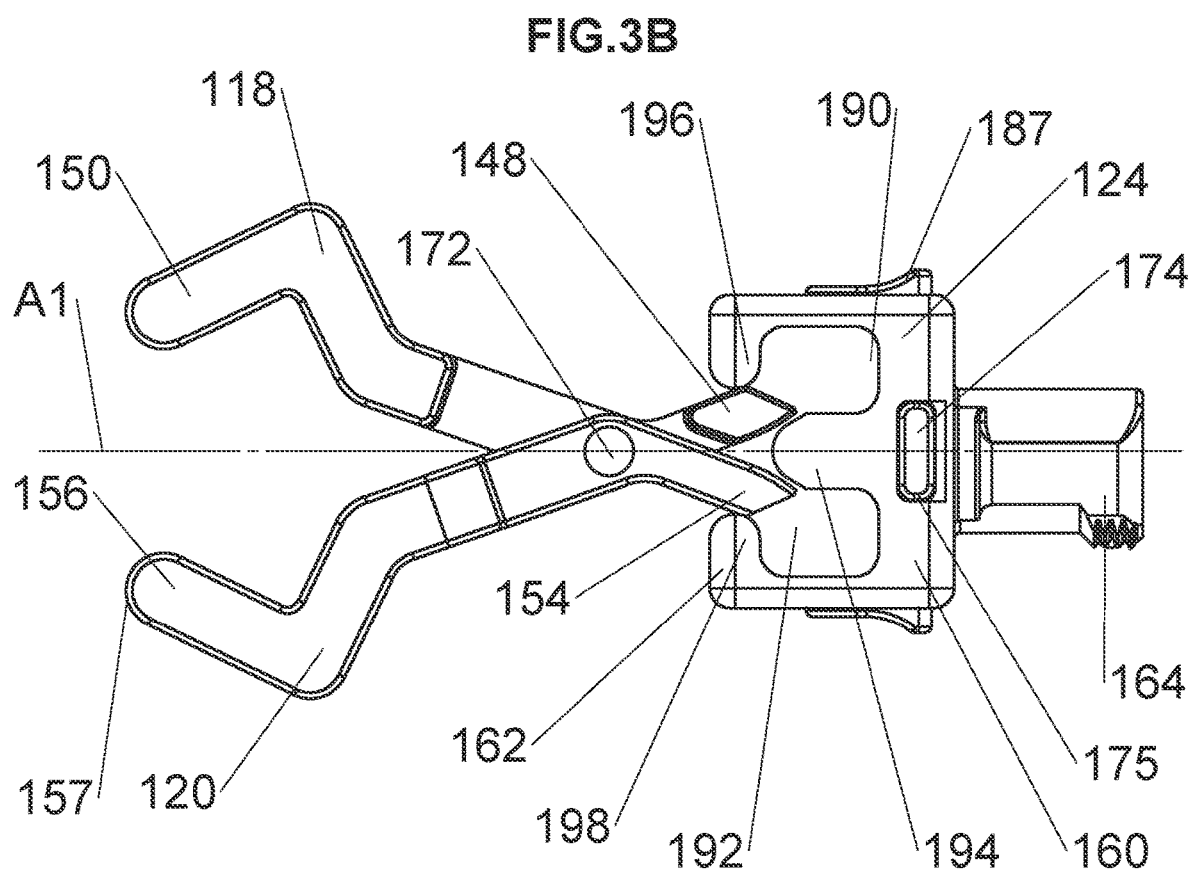

Distal                                                           Proximal

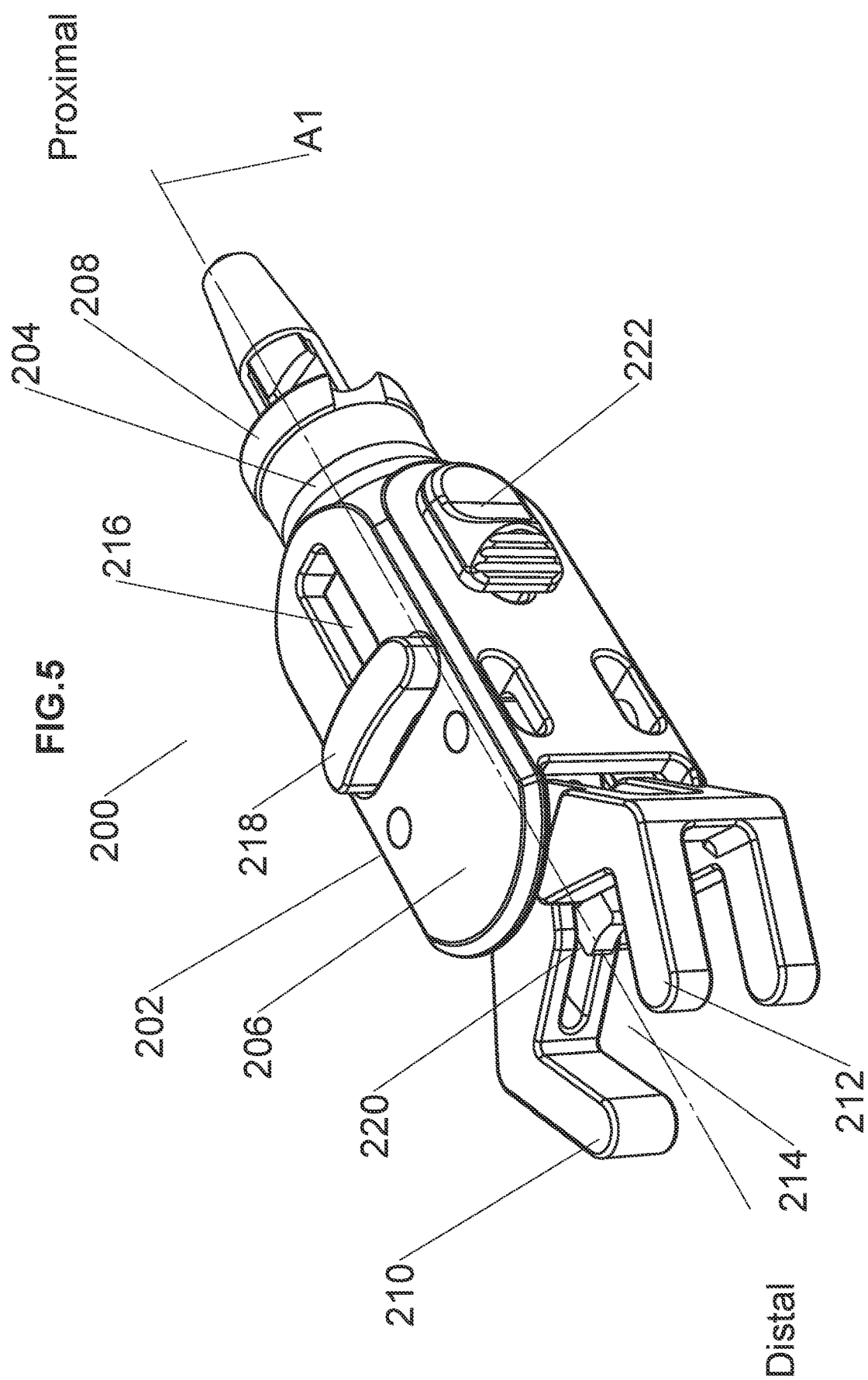

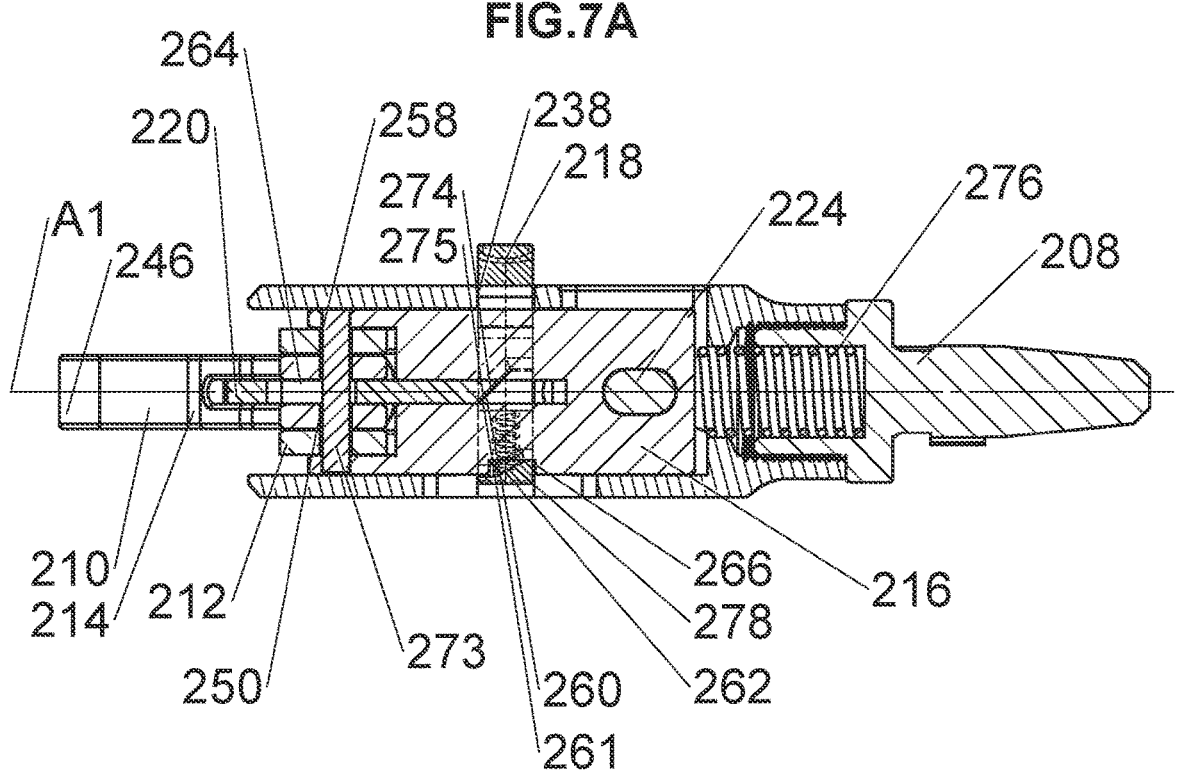
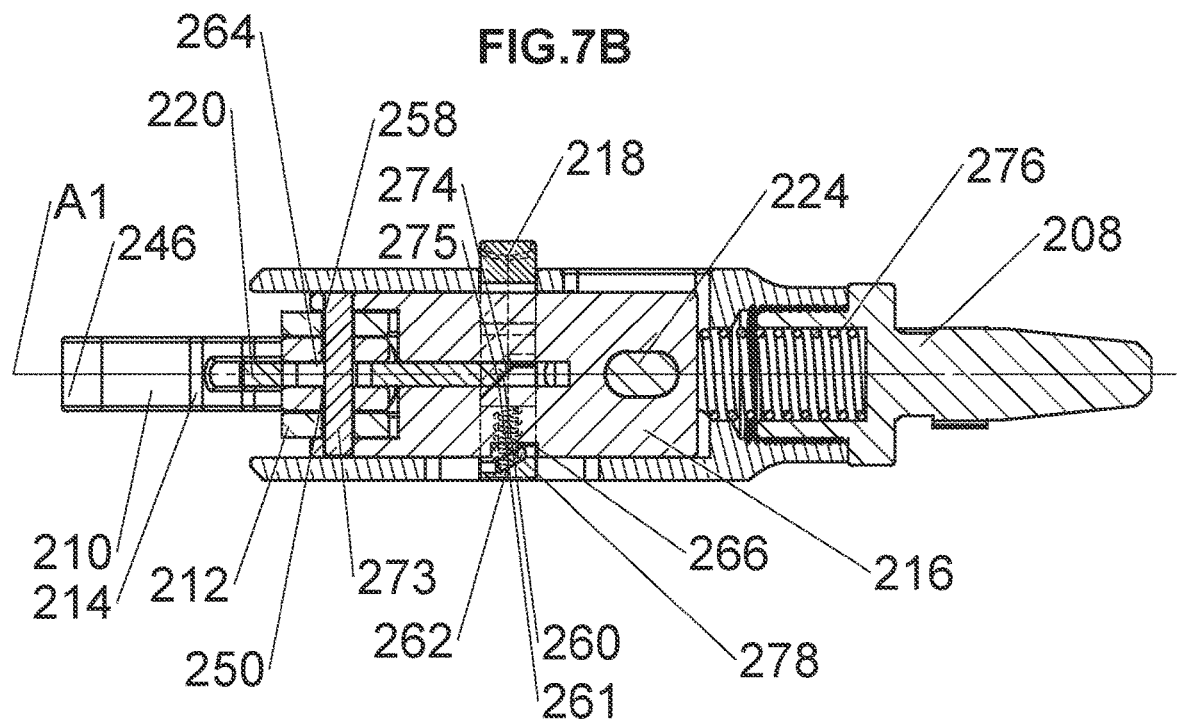

302
Engage proximal portion of housing with drive spring.

↓

304
Move lock to unlocked position to disengage the housing.

↓

306
Translate driving body proximally within housing to open jaws.

↓

308
Position surgical tool between jaws.

↓

310
Translate driving body distally within housing to close jaws.

END EFFECTOR FOR A SURGICAL ARM

CLAIM OF PRIORITY

This application claims the benefit of priority under 35 U.S.C. § 119(e) of U.S. Provisional Patent Application Ser. No. 62/990,275, filed on Mar. 16, 2020, which is herein incorporated by reference in its entirety.

BACKGROUND

The present invention relates generally to apparatus and systems for supporting surgical tools. Some surgical procedures include the use of a variety of surgical tools. In some of these procedures, it is required that the surgical tools be maintained in a single position for an extended period of time, such as an hour or more. Because it may be difficult or undesirable to manually hold a surgical tool for such a length of time, mechanical and/or electromechanical support (robotic) arms can be used to hold the position of a surgical tool while aspects of a surgical procedure are performed. Some robotic arms can be adjustable, such that a position of the arm can be adjusted before or during the surgical procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2 illustrates an exploded isometric view of the end effector, in accordance with at least one example of the present application.

FIG. 3A illustrates a side isometric view of the end effector in an open orientation, in accordance with at least one example of the present application.

FIG. 3B illustrates an isometric view of a driving body and a pair of jaws in an open orientation, in accordance with at least one example of the present application.

FIG. 5 illustrates an isometric view of an end effector, in accordance with at least one example of the present application.

FIG. 7A illustrates a cross-section view of an end effector in a first condition, in accordance with at least one example of the present application.

FIG. 7B illustrates a cross-section view of the end effector in a second condition, in accordance with at least one example of the present application.

FIG. 8 illustrates a flow chart of a method for using the end effector, in accordance with at least one example of the present application.

DETAILED DESCRIPTION

The following description and the drawings sufficiently illustrate specific examples to enable those skilled in the art to practice them. Other examples may incorporate structural, process, or other changes. Portions and features of some examples may be included in, or substituted for, those of other examples. Examples set forth in the claims encompass all available equivalents of those claims.

Various devices exist for retaining tools or instruments using surgical support arms (also referred to herein as robotic arms). However, in the operation of many such devices, two hands must be used in order to position, retain, or adjust a surgical tool within such a device. Additionally, many devices do not provide for adjustment of the surgical tool once a surgical tool is retained within the device. The devices and methods discussed herein are intended to address current disadvantages for some devices and techniques used for holding or retaining surgical tools in an end effector of a surgical support arm during a surgical procedure. The current disadvantages can be addressed by providing an end effector for a surgical arm capable of adjustably retaining a surgical tool between a pair of closable jaws, without requiring the use of a second hand. The end effector can also hold a variety surgical tools, and can also allow surgical tools to be withdrawn from between the pair of jaws without opening the pair of jaws.

In one example, the end effector can include a housing, a driving body translatable proximally and distally within the housing, and a drive spring to bias the driving body distally. In one example, the end effector can include a lock body which can retain the driving body in a distal position by engaging the housing and the driving body. The lock body can also be moved to an unlocked position to disengage the housing and release the driving body, to allow the drive spring to cause the driving body to translate to a distal position within the housing. In one or more examples, when the driving body translates proximally within the housing, the pair of jaws opens, and when the driving body translates distally within the housing, the pair of jaws closes. In one example, a surgical tool can be positioned between the pair of jaws to operate the lock body and release the driving body to close the pair of jaws and retain the surgical tool. The end effector can allow for one-handed securing and adjustable positioning of a surgical tool during a surgical procedure. One-handed retention and adjustment of a surgical tool can help save time during a surgical procedure and can also allow for a surgeon to complete certain aspects of a surgical procedure on their own rather than requiring the aid of an additional person.

Figure 1A:
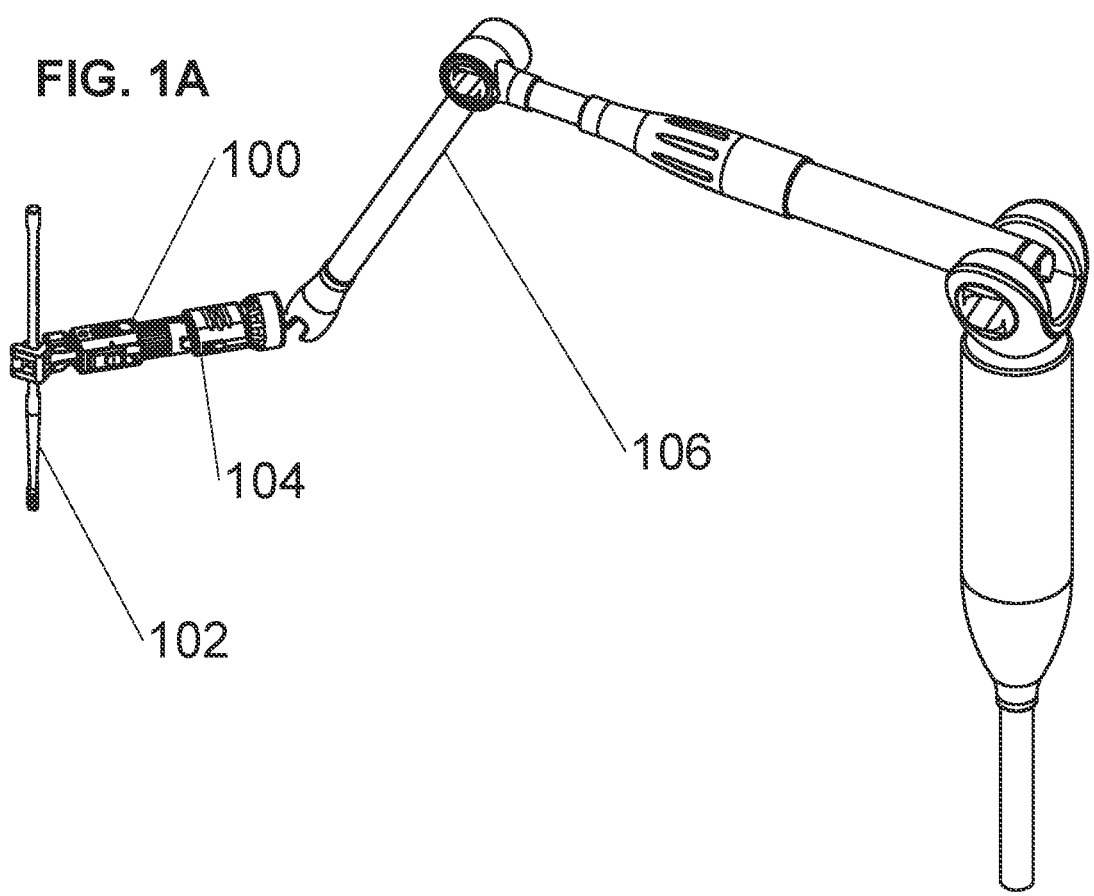
FIG. 1A illustrates an isometric view of an end effector retaining a surgical tool and coupled to a surgical arm, in accordance with at least one example of the present application.
Figure 1B:
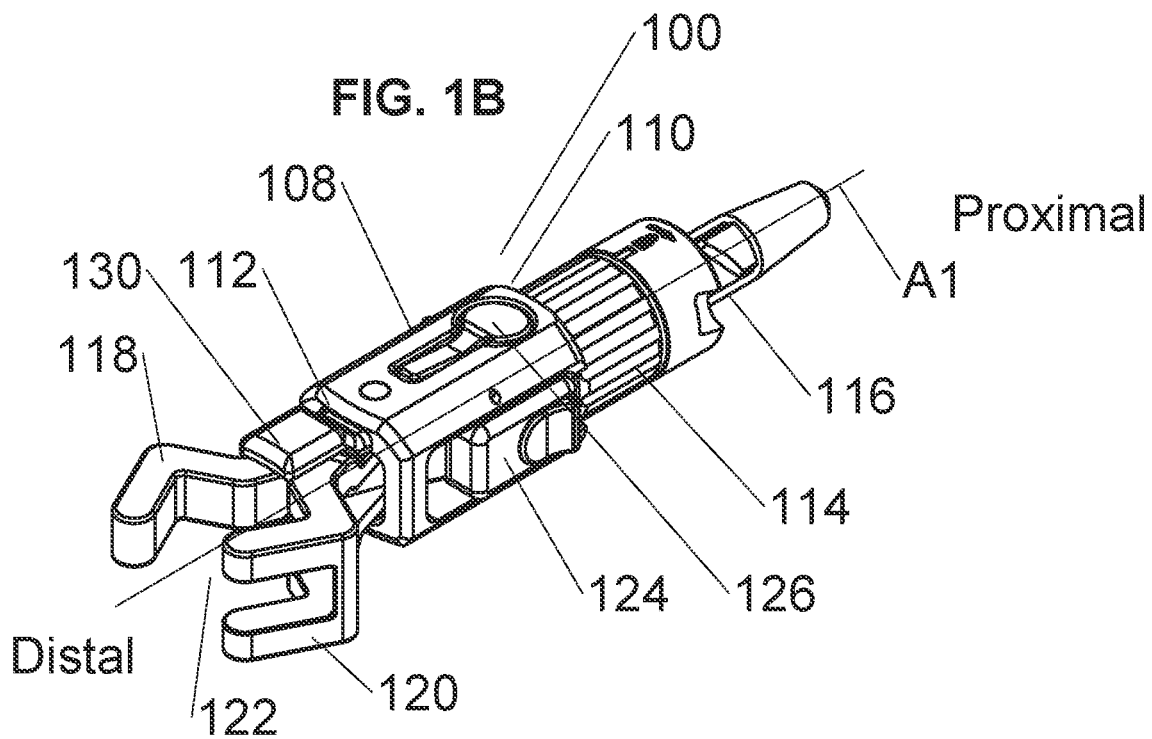
FIG. 1B illustrates an isometric view of the end effector, in accordance with at least one example of the present application.

FIG. 1A illustrates an isometric view of an end effector, in accordance with at least one example of the present application. FIG. 1B illustrates an isometric view of the end effector, in accordance with at least one example of the present application. Also shown in FIGS. 1A and 1B is a longitudinal axis A1, and orientation indicators Proximal and Distal. FIGS. 1A and 1B are discussed below concurrently.

As shown in FIG. 1A, the end effector 100 can be configured to hold and retain a surgical tool 102. The surgical tool 102 can be a variety of surgical tools or other instruments, such as a retractor, implant guide, implant trial device, implant inserter, drilling or cutting guide, or the like. The end effector coupler 104 can be configured to releasably couple the end effector 100 to the surgical arm 106. The surgical arm 106 can be used to adjustably position the end effector 100 and the surgical tool 102 during a surgical procedure when the end effector 100 is coupled to the end effector coupler 104 of the surgical arm 106.

As shown in FIG. 1B, the end effector 100 can include a housing 108 that can define a longitudinal axis A1. The housing 108 can include a proximal portion 110 and a distal portion 112. The end effector 100 can include a threaded collar 114 and a stem 116. The stem 116 can form a generally conical shape. The stem 116 can be configured to engage with the end effector coupler 104 to releasably couple the end effector 100 to the surgical arm 106. The stem 116 can also be configured to engage with other styles of pre-existing end effector couplers used with the surgical arm 106.

The threaded collar 114 and the stem 116 can be configured to engage the proximal portion 110 of the housing 108 to couple the threaded collar 114 and the stem 116 to the housing 108. The end effector 100 can include a first jaw 118 and a second jaw 120. The first jaw 118 and the second jaw 120 can extend outwardly from the distal portion 112 of the housing 108, and together define a tool opening 122. The first jaw 118 and the second jaw 120 can be pivotably coupled to the housing 108. The end effector 100 can include a driving body 124 positionable within the housing 108 and configured to translate within the housing 108 along the longitudinal axis A1. The driving body 124 can also be configured to engage the first jaw 118 and the second jaw 120.

The end effector 100 can include a lock 126 that can be pivotably coupled to the housing 108 to engage and disengage the driving body 124. The end effector 100 can also include a lock release 130. The lock release 130 can be positioned within the tool opening 122. The lock release 130 can be configured to be translated proximally by the surgical tool 102, when the surgical tool 102 is positioned between the first jaw 118 and the second jaw 120. In some examples, the end effector 100, various components can be made of materials not limited to, metals, plastics, foams, elastomers, ceramics, composites, combinations thereof, or the like.

In the operation of some examples, the end effector 100 can be coupled to an end effector coupler 104 of the surgical arm 106 in preparation for a surgical procedure. The surgical tool 102 can be positioned within the tool opening 122, between the first jaw 118 and the second jaw 120. The first jaw 118 and the second jaw 120 can pivot to close the tool opening 122 and retain the surgical instrument 102 via one-handed operation of the lock 126. The first jaw 118 and the second jaw 120 can pivot to open and close the tool opening 122, to retain the surgical tool 102 between the fist jaw 118 and the second jaw 120. The lock 126 can be configured to engage the driving body 124 and the housing 108. Operating the lock 126 can allow the driving body 124 to translate distally within the housing 108 to engage the first jaw 118 and the second jaw 120 and close the tool opening 122. The surgical tool 102 can be translated substantially orthogonally to the longitudinal axis A1, when the tool opening 122 is closed.

Alternatively, the surgical tool 102 can be positioned between the first jaw 118 and the second jaw 120 to contact the lock release 130. The lock release 130 can in turn contact the lock 126 to release the driving body 124 and close the tool opening 122 to retain the surgical tool 102 via one-handed operation. Following closure of the first jaw 118 and the second jaw 120 to secure the surgical tool 102, the surgical arm 106 can be adjusted to position the end effector 100 and the surgical tool 102 during a surgical procedure.

FIG. 2 illustrates an exploded view of an end effector, in accordance with at least one example of the present application. Also shown in FIG. 2 is a longitudinal axis A1, and orientation indicators Proximal and Distal. The threaded collar 114 can include gripping features 115 and female threads 117. The stem 116 can include a distal portion 131, threads 132, and a rotational lock 134. The housing 108 can include a threaded member 136, male threads 137, a transverse opening 138, a bore 140, a lock recess 142, a transverse slot 144, a top surface 143, a bottom portion 145, and a transverse bore 146. The first jaw 118 can include a proximal end 148, a distal end 150, and a bore 152. The second jaw 120 can include a proximal end 154, a first distal end 156, a second distal end 157, and a bore 158. The end effector 100 can include a friction element 168 and a friction spring 163. The threaded collar 114 can include a groove 165. The driving body 124 can include a proximal portion 160, a distal portion 162, a threaded member 164, a groove 165, and a bore 166. The end effector 100 can include a pin 172, a lock body 174, and a lock pin 178. The lock 126 can include a transverse bore 176 and a distal portion 180. The lock release 130 can include a proximal ramp 182 and an oblong bore 184. The end effector 100 can also include a drive spring 186 and a lock spring 188.

The end effector 100 can include the threaded collar 114. The threaded collar 114 can be generally cylindrical in shape. The gripping features 115 can extend from a surface of the threaded collar 114 in the form of protrusions, bumps, textured patterns, or the like. The threaded collar 114 can included the female threads 117. The female threads 117 can be configured to engage the threaded member 164 to couple the driving body 124 to the threaded collar 114.

The stem 116 can include the distal portion 131, threads 132, and the rotational lock 134. The threads 132 of the stem 116 can be formed within the distal portion 131 of the stem 116 and can be configured to engage the threaded member 136 of the housing 108 to couple the stem 116 to the housing 108. The rotational lock 134 can be a protrusion formed on an outer surface of the stem 116. The rotational lock 134 can be configured to rotatably engage with an end effector coupler used with surgical arms, in order to releasably couple the end effector 100 to a surgical arm, such as the surgical arm 106 of FIG. 1.

The proximal portion 110 and the opposite distal portion 112 can be proximal and distal portions of housing 108, respectively. The housing 108 can be an elongate body defining the longitudinal axis A1. The housing 108 can have a generally rectangular shape, but the housing 108 can also form other polygonal shapes in other examples. The threaded member 136 can extend proximally along the longitudinal axis A1 from the proximal portion 110. The threaded member 136 can form a generally cylindrical shape in some examples. The threaded member 136 can be configured to engage with the threads 132 of the stem 116.

The transverse opening 138 can be defined by the housing and can extend transversely through the housing 108 along the longitudinal axis A1. The transverse opening 138 can extend through the distal portion 112, the proximal portion 110, and the threaded member 136 of the housing 108. A proximal portion of the transverse opening 138 can be sized and shaped to retain the threaded member 136 therein and a distal portion of the transverse opening 138 can be sized and shaped to retain portions of the driving body 124, the first jaw 118, and the second jaw 120 therein.

The bore 140 of the housing can extend vertically though the top surface 143 and a bottom portion 145 of the distal portion 112 of the housing 108, substantially orthogonally to the longitudinal axis A1. The lock recess 142 can be a recess formed in the top surface 143 of the housing 108 near the bore 140. The lock recess 142 can generally extend along the longitudinal axis A1. The lock recess 142 can extend through the housing 108 to intersect the transverse opening 138. The lock recess 142 can be configured to accept the lock 126. When the lock 126 is positioned within the lock recess 142, a portion of the lock 126 can be flush with the top surface 143 of the housing 108. The transverse slot 144 can be a transverse bore formed within the lock recess 142. The transverse slot 144 can extend vertically through the housing 108 at the lock recess 142; and can intersect the transverse opening 138. The housing 108 can also include a bore 146, which can extend transversely through the housing 108 at the lock recess 142.

The proximal end 148 and the opposite distal end 150 can be proximal and distal ends of the first jaw 118, respectively. The proximal end 148 of the first jaw 118 can have a generally flattened, or rectangular prism shape. The proximal end 148 can also have a cuboid, trapezoidal, or other three-dimensional shape. The distal end 150 of the first jaw 118 can have a shape that can be configured to correspond to a surgical tool. The first jaw 118 can include the bore 152 that can extend vertically through the first jaw 118. Similarly, the proximal end 154 and the opposite first 156 and second 157 distal end can be proximal and distal end of the second jaw 120, respectively. The proximal end 154 of the second jaw 120 can also have a generally flattened, or rectangular prism shape. The proximal 154 of the second jaw 120 can also have a cuboid, trapezoidal, or other three-dimensional shape. The first distal end 156 and the second distal end 157 can have a shape that can be configured to correspond to a surgical tool. The second jaw 120 can include the bore 158, which can extend vertically through the second jaw 120. The first distal end 156 and the second distal end 157 can be vertically spaced to allow the distal end 150 of the first jaw 118 to pass between the first distal end 156 and the second distal end portion 157 when the first jaw 118 and the second jaw 120 are pivoted to close the tool opening.

The proximal portion 160 and the opposite distal portion 162 can be proximal and distal portions of the driving body 124, respectively. The driving body 124 can have a generally cuboid or rectangular shape between the proximal portion 160 and the distal portion 162. The threaded member 164 of the driving body can extend proximally along the longitudinal axis A1 and can form a generally cylindrical shape. The friction element 168 can have a generally cylindrical shape and can be configured to be insertable into the bore 166 of the driving body 124. The threaded collar 114 can include the groove 165. The groove can extend within the threaded collar 114 along the longitudinal axis A1. This friction element 168 can be positioned within the bore 166 of the driving body 124. The friction spring 163 can bias the friction element 168 outward from the bore 166 to engage the threaded collar 114. The friction element 168 can ride in the groove 165 of the collar 114 during proximal and distal translation of the driving body 124. When the threaded collar 114 is rotated, the friction element 168 can be forced inward to allow the threaded collar 114 to engage the threaded member 164 of the driving body 124; to retain the driving body in a proximal position within the housing 108. The friction spring 163 and the friction element 168 can also help to prevent accidental rotation of the threaded collar 114.

The driving body 124 can be configured to contact the housing 108, between the proximal portion 160 and the distal portion 162, within the transverse opening 138. The driving body 124 can be configured to translate proximally and distally within the transverse opening 138 along the longitudinal axis A1. The pin 172 can be configured to extend through the bore 140 in the distal portion of the housing 108. The pin 172 can include a larger diameter at one end, to limit vertical translation of the pin within the bore 140. The pin 172 can extend through bore 152 and the bore 158 of the first jaw 118 and the second jaw 120, respectively. The pin 172 can pivotably couple the first jaw 118 and the second jaw 120 to the distal portion 112 of the housing 108.

The end effector 100 can include the lock body 174. The lock body can have various shapes such as a rectangular prism, a cuboid, a sphere, a rounded three-dimensional shape, or other shape. The lock body 174 can be configured to be positioned in and extend through the transverse slot 144 in the lock recess 142 of the housing 108. The lock 126 can have a generally circular shape at a proximal portion and a generally rectangular at a distal portion; but can have other shapes in other examples. The lock 126 can be positionable at least partially within the lock recess 142. The transverse bore 187 can extend through the proximal portion of the lock 126 and can be configured to accept the pin 178. The pin 178 can pivotably couple the lock 126 to the housing 108 when the pin 178 is inserted through the bore 146 in the housing 108 and through the transverse bore 176 in the lock 126.

The distal portion 180 can be a chamfer or bevel formed in a generally distal portion of the lock 126. The lock release 130 can include the proximal ramp 182. The proximal ramp 182 can be configured to correspondingly engage the distal portion 180 of the lock 126. The oblong bore 184 can be configured to allow the pin 172 to pass through the lock release 130. The oblong bore 184 can allow and guide proximal and distal translation of the lock release 130 with respect to the housing 108 when the pin 172 is inserted through the housing 108 and the lock release 130. When the lock release 130 is translated distally, the proximal ramp 182 can engage the distal portion 180 of the lock 126 to pivot the lock 126.

The drive spring 186 can be a spring, such as a coil compression spring, but can be other biasing or resilient members, such as a wave spring or compressible and resilient members comprised of resilient materials such as rubbers, plastic, or the like. The drive spring 186 can be positioned at least partially within the threaded member 136 of the housing 108, and can extend along the longitudinal axis A1. When the drive spring 186 is positioned, a proximally orientated end can contact the stem 116, and a distally oriented end can contact the driving body 124 within the threaded member 136. The drive spring 186 can extend within the threaded collar 114, between the stem 116 and the threaded member 136, when the threaded collar 114 is engaged with the threaded member 136 of the housing 108. The drive spring 186 can be operable to bias the driving body 124 distally to close the first jaw 118 and the second jaw 120. The lock spring 188 can be a compression spring such as a coil compression spring, but can be other biasing or resilient members, such as a wave spring or compressible and resilient members comprised of resilient materials such as rubbers, plastic, or the like. The lock spring 188 can be positioned within the driving body 124 to bias the lock body 174 vertically to extend into the transverse slot 144 of the housing 108, in order to engage the housing 108 to lock the driving body 124 in a proximal position within the housing 108.

Figure 3C:
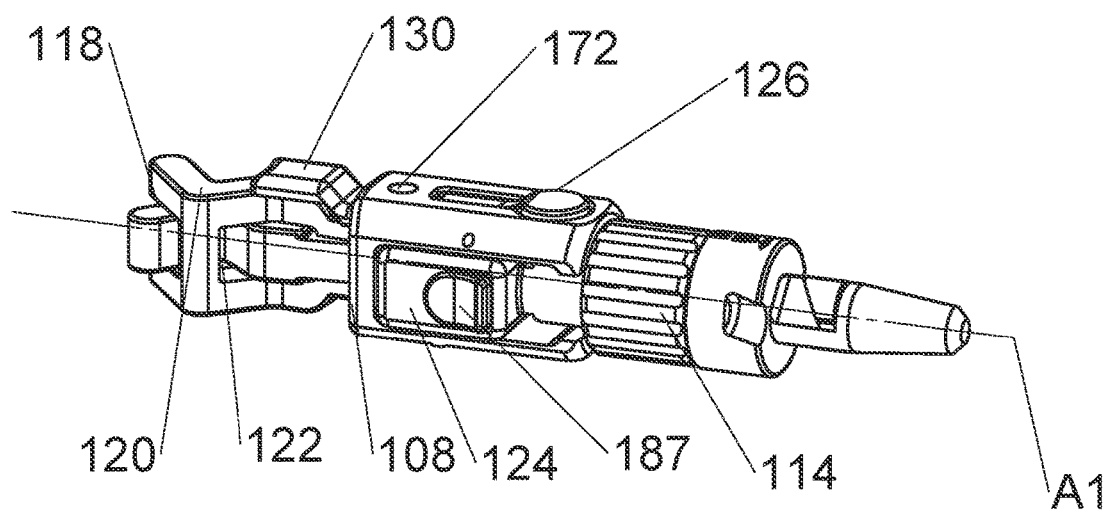
FIG. 3C illustrates a side isometric view of the end effector in a closed orientation, in accordance with at least one example of the present application.
Figure 3D:
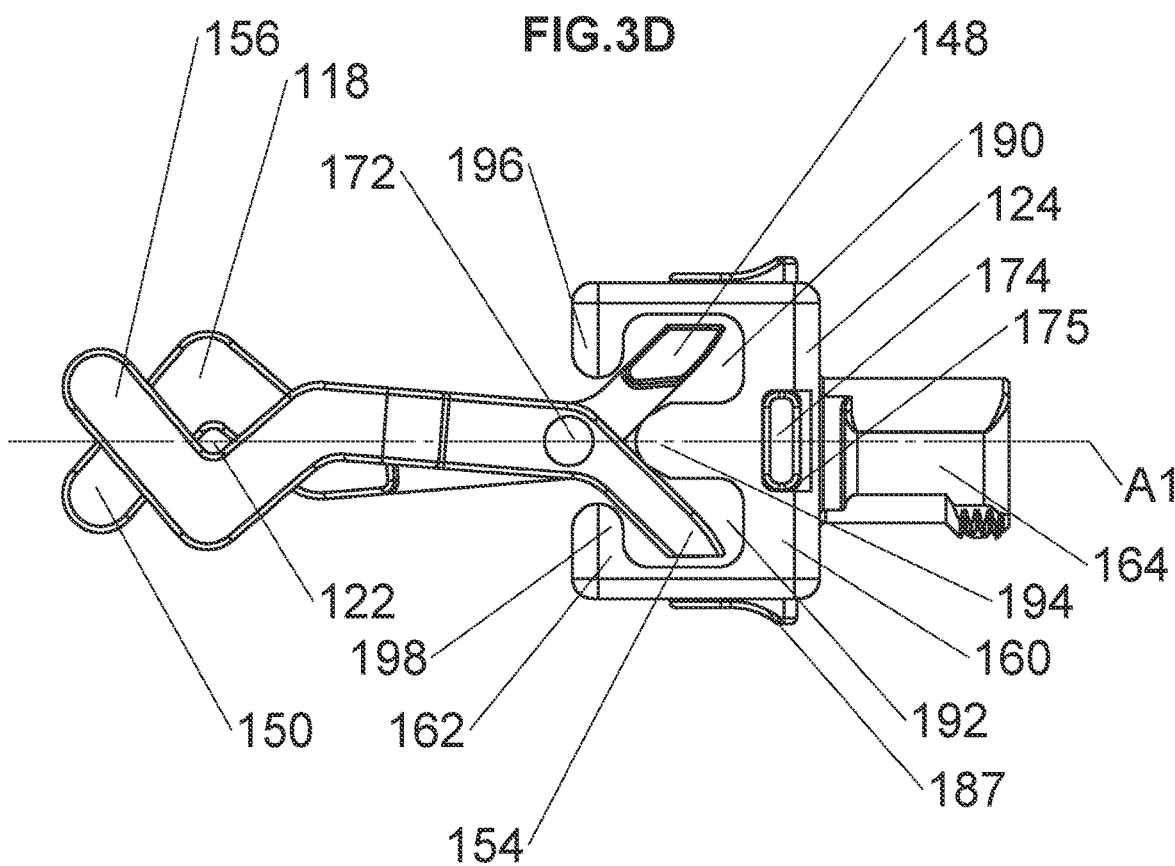
FIG. 3D illustrates an isometric view of the driving body and the pair of jaws in a closed orientation, in accordance with at least one example of the present application.

Further details and operation of the end effector 100 are discussed below with respect to FIGS. 3A-3D. FIG. 3A illustrates a side isometric view of the end effector in an open orientation, in accordance with at least one example of the present application. FIG. 3B illustrates an isometric view of a driving body and a pair of jaws in an open orientation, in accordance with at least one example of the present application. FIG. 3C illustrates a side isometric view of the end effector in a closed orientation, in accordance with at least one example of the present application. FIG. 3D illustrates an isometric view of the driving body and the pair of jaws in a closed orientation, in accordance with at least one example of the present application. FIGS. 3A-3D also illustrate a longitudinal axis A1 and orientation indicators Proximal and Distal. FIGS. 3A-3D are discussed below concurrently.

The lock body cavity 175 can be configured to accept the lock body 174. When the lock body 174 is positioned within the lock cavity 175, the lock body 174 can extend substantially orthogonally to the longitudinal axis A1. The lock body 174 can extend from the lock cavity 175 and engage the housing 108 to limit distal translation of the driving body 124. Additionally, the threaded collar 114 can be threadably engageable with the threaded member 164 of the driving body 124, to allow for additional manual adjustment of the driving body within the housing 108. For example, rotation of the treaded collar 114 can cause proximal translation, to further open the first jaw 118 and the second jaw 120 and limit distal translation of the driving body 124, and distal translation of the driving body 124, to increase the force applied to the first jaw 118 and the second jaw 120; depending on the direction the treaded collar 114 is rotated. The driving body 124 can also include the protrusions 187, which can extend laterally outward from the driving body 124 to increase the grip a user has on the driving body 124. Accordingly, the protrusions 187 can aid in manually translating the driving body 124 proximally along the longitudinal axis A1.

As shown in FIG. 3A, the tool opening 122 can be open when the driving body 124 is in a proximal position within the housing 108. The guide protrusion 194 can be a portion of the driving body 124 aligned with, and extending along, the longitudinal axis A1. The first arm 196 and the second arm 198 can be portions of the driving body extending laterally inward from outer portions of the driving body 124. In some examples, the first arm 196 and the second arm 198 can extend inwardly substantially orthogonally to the longitudinal axis A1. The guide protrusion 194, the first arm 196, and the second arm 198 can together define the first opening 190 and the second opening 192. The first opening 190 can extend longitudinally within the driving body 124, from the first arm 196 at the proximal portion 160 to near the distal portion 162, and laterally outward from the guide protrusion 194 to near outer portions of the driving body 124. The first opening 190 can have a generally cuboid or rectangular shape with rounded corners. The second opening 192 of the drive body 124 can extend longitudinally within the driving body 124 from the second arm 198 at the proximal portion 160, to near the distal portion 162, and laterally outward from the guide protrusion 194 to near outer portions of the driving body 124. The second opening 192 can have a generally cuboid or rectangular shape with rounded corners.

The guide protrusion 194 can substantially separate the first opening 190 from the second opening 192. The guide protrusion 194 and the first arm 196 can be configured to contact and guide the proximal end 148 of the first jaw 118 and the guide protrusion 194 and the second arm 198 can be configured to contact and guide the proximal end 154 of the second jaw 120 when the driving body 124 is translated distally within the housing 108 to close the distal ends 150, 156, and 157, respectively, and to close the tool opening 122. The first opening 190 can be configured to accept the proximal end 148 of the first jaw 118 and the second opening 192 can be configured to accept the proximal end 154 of the second jaw 120.

For example, when the first jaw 118 contacts the guide protrusion 194 during distal translation, the guide protrusion causes the proximal end 148 of the first jaw 118 to move laterally outward, causing the first jaw 118 to pivot about the pin 172, and further causing the distal end 150 to move toward the longitudinal axis A1, toward the closed position. Contact between the proximal end 148 of the first jaw 118 and the first arm 196 during distal translation of the driving body 124 can guide the proximal end 148 into the first opening 190, and limit laterally outward movement of the proximal end 148, to help provide linear and consistent movement of the first jaw 118 toward the closed position. When the first jaw 118 contacts the guide protrusion 194 during proximal translation, the guide protrusion 194 causes the proximal end 148 of the first arm 118 to move laterally inward, causing the first jaw 118 to pivot about the pin 172, and further causing the distal end 150 to move away from the longitudinal axis A1 toward the open position. When the second jaw 120 contacts the guide protrusion 194 during distal translation, the guide protrusion 194 causes the proximal end 154 of the second jaw 120 to move laterally outward, causing the second jaw 120 to pivot about the pin 172, and further causing the distal ends 156 and 157 to move toward the longitudinal axis A1, toward the closed position. Contact between the proximal end 154 of the second jaw 120 and the second arm 198 during distal translation of the driving body 124 can guide the proximal end 154 into the second opening 192 and limit laterally outward movement of the proximal end 154, to help provide linear and consistent movement of the second jaw 120 toward the closed position.

Contact between the proximal end 148 of the first jaw 118 and the first arm 196 during proximal translation of the driving body 124 can guide the proximal end 148 out of the opening 190, and contact between the proximal end 148 and the guide protrusion 194 can limit laterally inward movement of the proximal end 148 to help provide linear and consistent movement of the first jaw 118 jaw toward the open position.

When the second jaw 120 contacts the guide protrusion 194 during proximal translation, the guide protrusion 194 causes the proximal end 154 of the second jaw 120 to move laterally inward, causing the second jaw 120 to pivot about the pin 172, and further causing the distal ends 156 and 157 to move away from the longitudinal axis A1 toward the open position. Contact between the proximal end 154 of the second jaw 120 and the second arm 198 during proximal translation of the driving body 124 can guide the proximal end 154 out of the second opening 192, and contact between the proximal end 154 and the guide protrusion 194 can limit laterally inward movement of the proximal end 154, to help provide linear and consistent movement of the second jaw 120 toward the open position. Accordingly, when the driving body 124 is in a proximal position, as shown in FIGS. 3A-3B, the tool opening 122 is open. When the driving body 124 is in a distal position, as shown in FIG. 3C-3D, the tool opening 122 is closed.

Figure 4A:
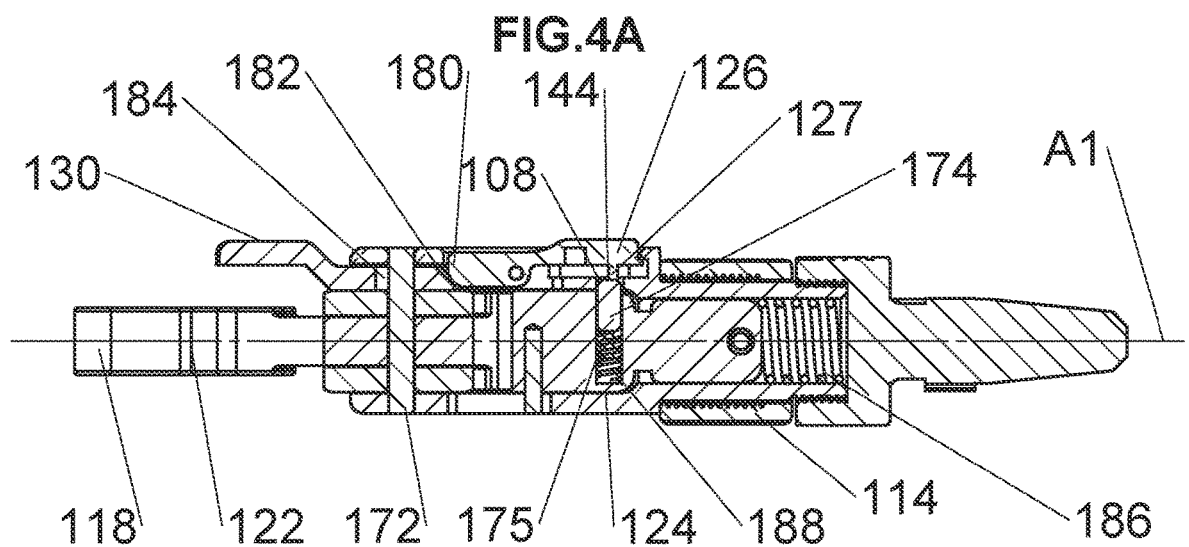
FIG. 4A illustrates a cross-section view of the end effector in a first condition, in accordance with at least one example of the present application.
Figure 4B:
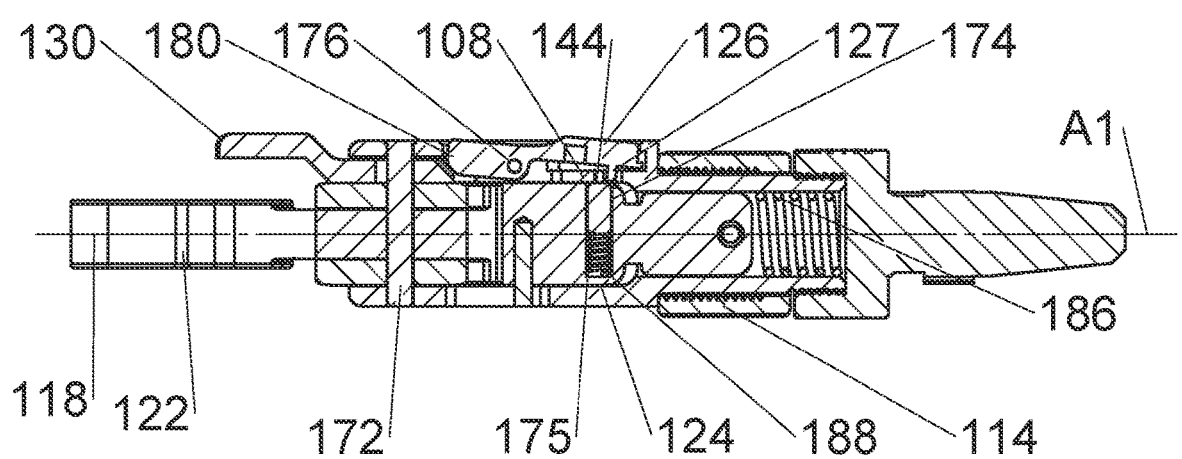
FIG. 4B illustrates a cross-section view of the end effector in a second condition, in accordance with at least one example of the present application.
Figure 4C:
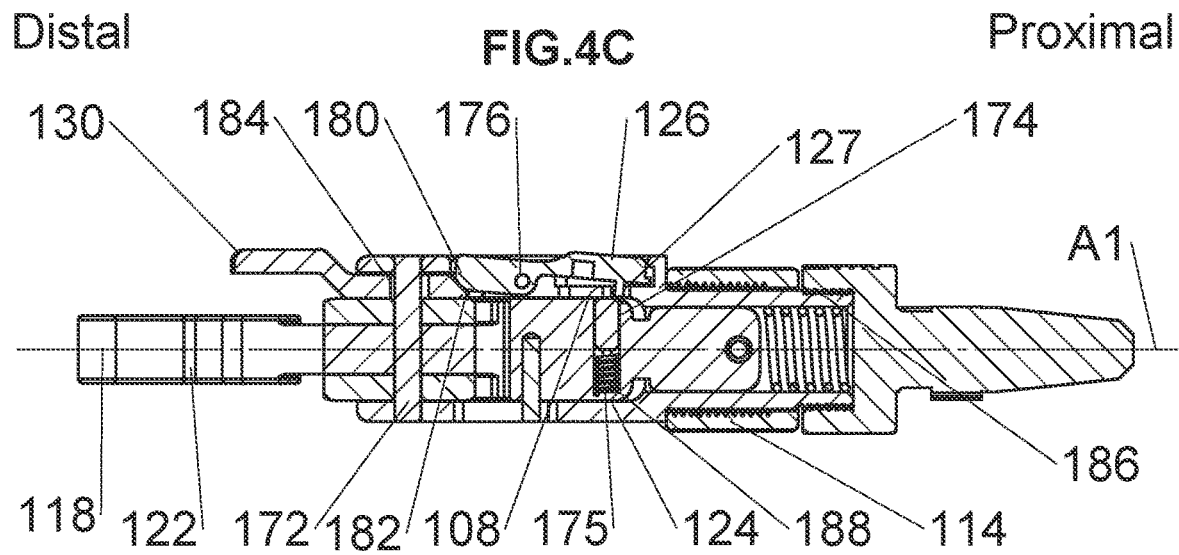
FIG. 4C illustrates a cross-section view of the end effector in a third condition, in accordance with at least one example of the present application.

FIGS. 4A-4C illustrate cross-section views of the end effector in a first, a second, and a third condition, respectively, in accordance with various examples of the present application. FIGS. 4A-4C also show a longitudinal axis A1. FIGS. 4A-4C are discussed below concurrently.

FIG. 4A shows that end effector 100 can be in a locked condition. In the locked condition, the driving body 124 can be retained in a proximal position within the housing 108, and the first jaw 118 and the second jaw 120 can be open. The lock spring 188 can be in a resting state and the drive spring 186 can be in a compressed state. In the resting state, the lock spring 188 can still be partially compressed in order to maintain some force to bias the lock body 174 vertically to engage the housing 108. The lock 126 can extend generally parallel to the longitudinal axis A1. The lock spring 188 can bias the lock body 174 vertically to extend beyond the lock cavity 175 in the transverse slot 144 to engage the housing 108 and to engage the lock projection 127. The lock body 174 can also be positioned in the lock cavity 175 to engage the drive body 124 to prevent relative movement of the drive body 124 to the housing 108, helping to hold the drive body 124 in the proximal position, and the first jaw 118 and the second jaw 120 in the open position.

FIG. 4B shows a first example of how the end effector 100 can be in an unlocked condition. FIG. 4B shows that the lock 126 can include a lock projection 127, which can extend downward from a body of the lock 126 and can be configured to extend through the transverse slot 144 of the housing 108 to engage the lock body 174. FIG. 4B also shows that the lock 126 can be operated to release the driving body 124 and close the first jaw 118 and the second jaw 120. In the unlocked condition, the lock spring 188 can be in a compressed state and the driving spring 186 can be in resting state.

The lock 126 can include the lock projection 127. The lock projection 127 can be configured to extend through the transverse slot 144 of the housing 108, to engage the lock body 174. In operation, the lock 126 can be operated by applying a downward force on the lock 126 to cause the lock 126 to pivot toward the lock body 174. When pivoted, the lock 126 can move toward the longitudinal axis A1. When the lock 126 is pivoted, the lock projection 127 can contact and translate the lock body 174 into the lock cavity 175, compressing the lock spring 188, so that the lock body 174 is disengaged from the transverse slot 144 of the housing 108, releasing the driving body 124 from the housing 108. Once the driving body 124 is released from engagement with the housing 108, the drive spring 186 can drive the driving body 124 distally within the housing 108 to close the first jaw 118 and the second jaw 120, as described above with respect to FIGS. 3A-3C. The drive spring 186 can be in resting state once the driving body 124 has translated distally and closed the tool opening 122. In some examples, in the resting state, the drive spring 186 can still be partially compressed in order to maintain some force to hold the driving body 124 in the distal position.

FIG. 4C shows a second example of how the end effector 100 can be operated to close the first jaw 118 and the second jaw 120 by operating the lock release 130 to release the driving body 124 to close the tool opening 122. The lock release 130 can be operated by translating proximally relative to the housing 108, for example, by a surgical tool positioned within the tool opening 122. The oblong bore 184 can allow the lock release 130 to translate proximally and distally around the pin 172. The pin 172 can accordingly limit proximal and distal translation of the lock release 130.

The proximal ramp can engage the distal portion 180 to cause upward movement of the distal portion 180, causing the lock 126 to pivot to translate the lock body 174 into the lock cavity 175. The driving body 124 can then be released from the housing 108 once the lock body 124 translates sufficiently into the lock cavity 175 such that the lock body 174 is disengaged from the transverse slot 144 of the housing 108. Once the lock body 174 is released from the housing 108, the drive spring 186 can drive the driving body 124 to translate distally within the housing 108 to close the first jaw 118 and the second jaw 120.

When it is desired to re-open the first jaw 118 and the second jaw 120, the end effector 100 can be returned to the locked condition through proximal translation of the driving body 124, such as by using the projections 187 to translate the driving body 124 proximally to overcome the force of the drive spring 186, until the lock body 174 is aligned with the transverse slot 144; allowing the lock spring 188 to drive the lock body 174 vertically to enter the transverse slot 144 and engage the housing 108 to limit translation of the lock body 124 with respect to the housing 108. Such a process can be repeated, as desired.

The ability of the lock 126 to be operated to close the tool opening 122 by both direct operation and by indirect operation through the lock release 130 can provide a user with two separate methods to retain a surgical tool within the tool opening 122 using only a single hand. This ability of the end effector 100 can be advantageous during surgical operations where a surgeon may not be able to use two hands or may not be able to manually operate the lock 126, due to, for example, simultaneously holding a surgical tool in the tool opening 122. This ability can also save time during surgical operations.

FIG. 5 illustrates an isometric view of an end effector, in accordance with at least one example of the present application. Also shown in FIG. 5 is a longitudinal axis A1, and orientation indicators Proximal and Distal. The end effector 200 can include a housing 202 that can define a longitudinal axis A1. The housing 202 can include a proximal portion 204 and a distal portion 206. The end effector 200 can include a stem 208. The stem 208 can be generally conical in shape. The stem 208 can be coupled to the proximal portion 204 of the housing 202. The stem 208 can be configured to engage with pre-existing end effector couplers to releasably couple the end effector 200 to a surgical arm.

The end effector 200 can include a first jaw 210 and a second jaw 212. The first jaw 210 and the second jaw 212 can extend outwardly from the distal portion 206 of the housing 202, and together define a tool opening 214. The first jaw 210 and the second jaw 212 can be pivotably coupled to the housing 202. The end effector 200 can include a driving body 216 positionable within the housing 202 and configured to translate within the housing 202 along the longitudinal axis A1. The driving body 216 can also be configured to engage the first jaw 210 and the second jaw 212.

The end effector 200 can include a lock 218. The lock 218 can be retained, and can translate vertically within, the housing 202. In some examples, the lock 218 can translate substantially orthogonally to the longitudinal axis A1. The lock 218 can translate vertically within the housing 202 to engage and disengage the driving body 216. The end effector 200 can include a lock release 220. The lock release 220 can be positioned within the tool opening 214. The lock release 220 can be configured to be translated proximally by a surgical tool, when a surgical tool is positioned between the first jaw 210 and the second jaw 212. The end effector can include a first projection 222. The first projection 222 can be operable to translate the driving body 216 proximally within the housing 202. In some examples, the end effector 200, various components can be made of materials not limited to, metals, plastics, foams, elastomers, ceramics, composites, combinations thereof, or the like.

In the operation of some examples, the end effector 200 can be coupled to an end effector of a surgical arm in preparation for a surgical procedure. A surgical tool can be positioned within the tool opening 214, between the first jaw 210 and the second jaw 212. The first jaw 210 and the second jaw 212 can pivot to close the tool opening 214 and retain a surgical tool via one-handed operation of the lock 218. The lock 218 can be configured to engage the driving body 216 within the housing 202. Operating the lock 218 can allow the driving body 216 to translate distally within the housing 202 to engage the first jaw 210 and the second jaw 212 and close the tool opening 214. A surgical tool can be translated substantially orthogonally to the longitudinal axis A1, when the tool opening 214 is closed.

Alternatively, a surgical tool can be positioned between the first jaw 210 and the second jaw 212 to contact the lock release 220. The lock release 220 can in turn contact the lock 218 to release the driving body 216 and close the tool opening 214 to retain a surgical tool via one-handed operation. Following closure of the first jaw 210 and the second jaw 212 to secure a surgical tool, the surgical arm can be adjusted to position the end effector 200 and a secured surgical tool during a surgical procedure.

Figure 6:
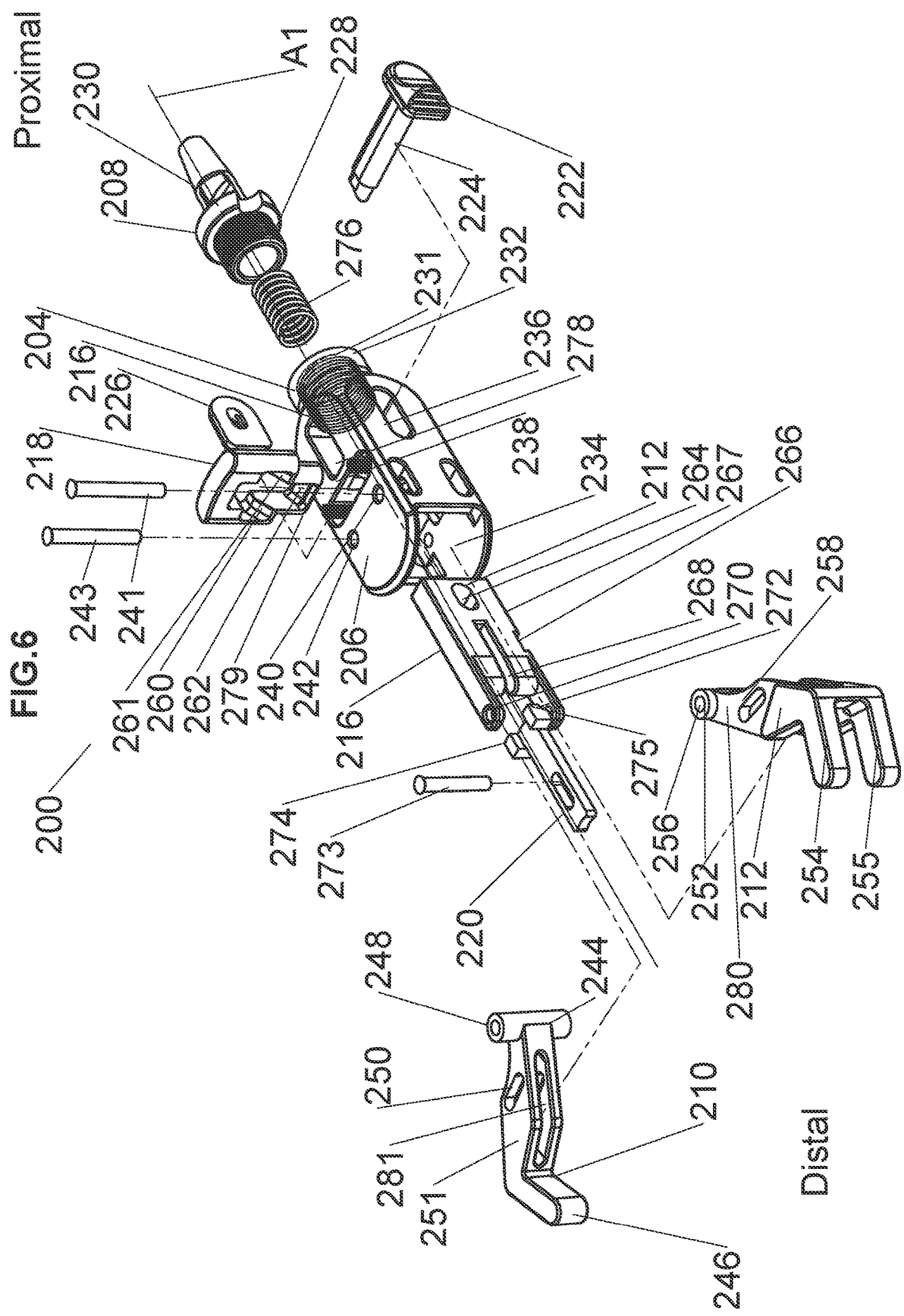
FIG. 6 illustrates an exploded view of an end effector, in accordance with at least one example of the present application.

FIG. 6 illustrates an exploded view of the end effector, in accordance with at least one example of the present application. Also shown in FIG. 6 is a longitudinal axis A1, and orientation indicators Proximal and Distal. The end effector 200 can include a transverse body 224, a second protrusion 226, male threads 228, a rotational lock 230, female threads 231, a threaded member 232, an opening 234, a transverse opening 236, a lock opening 238, a first bore 240, a first pin 241, a second bore 242, and a second pin 243. The first jaw 210 can include a proximal end 244, a distal end 246, a bore 248, a guide groove 250, an opening 281, and a superior surface 251. The second jaw 212 can include a proximal end 252, a first distal end 254, a second distal end 255, a bore 256, a guide groove 258, a superior surface 280, and an inferior surface 259. The lock 218 can include a first superior ramp 260, a second superior ramp 261, and an inferior ramp 262. The driving body 216 can include a transverse bore 264, a lock recess 266, an inferior surface 267, a groove 268, a superior bore 270, and an inferior bore 272. The lock release 220 can include a first proximal ramp 274 and a second proximal ramp 275. The end effector 200 can also include a can include a third pin 273, a drive spring 276, a first lock spring 277, and a second lock spring 278.

The transverse body 224 can extend transversely through the housing 202, substantially orthogonally to the longitudinal axis A1. The first projection 222 and the second protrusion 226 can extend laterally outwardly beyond the housing 202. The first projection 222 and the second protrusion 226 can coupled to the transverse body 224, on opposite sides of outer portions of the housing 202. The first projection 222 and the second protrusion 226 can be operable translate the transverse body 224 proximally along the longitudinal axis A1, within the housing 202. The stem 208 can include the male threads 228. The male threads 228 can be configured to engage the female threads 231 of the threaded member 232 to couple the stem 208 to the housing 202. The rotational lock 230 can be a protrusion formed on an outer surface of the stem 208. The rotational lock 230 can be configured to rotatably engage with an end effector coupler used with surgical arms, in order to releasably couple the end effector 200 to a surgical arm, such as the surgical arm shown in FIG. 1.

The proximal portion 204 and the opposite distal portion 206 can be proximal and distal portions of housing 202, respectively. The housing 202 can be an elongate body defining the longitudinal axis A1. The housing 202 can have a generally rectangular shape, but the housing 202 can also form other polygonal shapes in other examples. The threaded member 232 can extend proximally along the longitudinal axis A1 from the proximal portion 204. The threaded member 232 can form a generally cylindrical shape in some examples. The female threads 231 of the threaded member 232 can be configured to engage with the male threads 228 of the stem 208.

The opening 234 can be defined by the housing 202 and can extend transversely along the longitudinal axis A1. The opening 234 can extend through the distal portion 206, proximal portion 204, and the threaded member 232 of the housing 202. The transverse opening 236 can extend transversely through the housing 208 generally between proximal portion 204 and the distal portion 206. The lock opening 238 can extend vertically through the housing generally between the proximal portion 204 and the distal portion 206. The first bore 240 and the second bore 242 can extend vertically through the distal portion 206 of the housing 202, substantially orthogonally to longitudinal axis A1. The first pin 241 and the second pin 243 can be configured to be received within, and extend through, the first bore 240 and the second bore 242.

The proximal end 244 and the opposite distal end 246 can be proximal and distal ends of the first jaw 210, respectively. The proximal end 244 of the first jaw 210 can have a generally cylindrical shape in some examples. The distal portion 246 of the first jaw 210 can have a shape that can be configured to correspond to a surgical tool. The bore 248 can extend vertically through the first jaw 210. The bore 248 can be configured to accept the first pin 241 to pivotably couple the first jaw 210 to the distal portion 206 of the housing 202. The guide groove 250 can extend vertically through the superior surface 251 of the first jaw 210.

The proximal end 252 and the opposite first 254 and second 255 distal ends can be proximal and distal ends of the second jaw 212, respectively. The proximal end 252 of the second jaw 212 can have a generally cylindrical shape in some examples. The first distal end 254 and the second distal end 255 of the second jaw 212 can have a shape that can be configured to correspond to a surgical tool. The first distal end 254 and the second distal end 255 can be spaced allow the distal end 246 of the first jaw 210 to extend between the first distal end 254 and the second distal end 255, when the first jaw 210 and the second jaw 212 are closed. The bore 256 can extend vertically through the second jaw 212. The bore 256 can be configured to accept the second pin 243 to pivotably couple the second jaw 212 to the distal portion 206 of the housing 202. The guide groove 258 can extend vertically through the superior surface 280 of the second jaw 212.

The driving body 216 can have a generally flattened, or rectangular prism shape. The driving body 216 can also have other three-dimensional shapes. The driving body 216 can extend along the longitudinal axis A1. The driving body 216 can be configured to contact the housing 202 between the proximal portion 204 and the distal portion 206, within the opening 234. The driving body 216 can be configured to translate proximally and distally within the opening 234 along the longitudinal axis A1. The transverse opening 236 can extend transversely through the housing 202 to intersect with the opening 234. The transverse opening 236 can be configured to accept the transverse body 224. The transverse body 224 can engage and translate the driving body 216 proximally and distally within the transverse opening 236. The lock recess 266 can be a chamfer or bevel formed in an inferior surface 267 of the driving body 216. The lock recess 266 can be configured to engage the lock body 218.

The guide groove 250 of the first jaw 210 and the guide groove 258 of the second jaw 212 can be configured to accept the third pin 273. The third pin 273 can be positioned within the superior bore 270 and the inferior bore 272 of the driving body 216. The superior bore 270, the inferior bore 272, the guide groove 250, and the guide groove 258 can together guide the pivoting motion of the first jaw 210 and the second jaw 212, respectively, when the first jaw 210 and the second jaw 212 pivot through contact by the driving body 216.

The groove 268 can extend within the driving body 216, substantially parallel to the longitudinal axis A1. The groove 268 can be configured to accept the lock release 220. The groove 268 can guide proximal and distal translation of the lock release 220 within the driving body 216. The lock release 220 can include the first proximal ramp 274 and the second proximal ramp 275. The first proximal ramp 274 and the second proximal ramp 275 can be chamfers or bevels formed in a generally proximal portions of the lock release 220. The first proximal ramp 274 and the second proximal ramp 275 can be configured to engage the corresponding first superior ramp 260 and the second superior ramp 261 of the lock body 218.

When the lock release 220 is translated proximally through contact from a surgical tool, the first proximal ramp 274 and the second proximal ramp 275 can engage the first superior ramp 260 and the second superior ramp 261, respectively, to translate the lock body 218 vertically downward and release the driving body 216. In some examples, the lock body 118 can translate substantially orthogonally to the longitudinal axis A1. The inferior ramp 262 of the lock body 218 can be configured to engage the lock recess 266 of the driving body 216, to retain the driving body 216 in a proximal position within the housing 202. The lock body 218 can be can depressed to disengage the inferior ramp 262 from the lock recess 266 of the driving body 216 to release the driving body 216.

The drive spring 276 can be a compression spring, such as a coil compression spring, but can be other biasing or resilient members, such as a wave spring or compressible and resilient members comprised of resilient materials such as rubbers, plastic, or the like. The drive spring 276 can be positioned at least partially within the threaded member 232 of the housing 202 and can extend along the longitudinal axis A1. When the drive spring 276 is positioned, a proximally oriented end of the drive spring 276 can contact the stem 208, and a distally oriented end can contact the driving body 216. The drive spring 276 can be operable to bias the driving body 216 distally to close the first jaw 210 and the second jaw 212. The first lock spring 277 and the second lock spring 278 can be compression springs, such as coil compression springs, but can also be other biasing or resilient members, such as wave springs or compressible and resilient members comprised of resilient materials such as rubbers, plastics, or the like. The first lock spring 277 and the second lock spring 278 can be positioned beneath the lock body 218 within the opening 234 of the housing 202. The first lock spring 277 and the second lock spring 278 can extend substantially orthogonally to the longitudinal axis A1. When positioned, the first lock spring 277 and the second lock spring 278 can together bias the lock body 218 vertically to cause the inferior ramp 262 to engage the lock recess 266 of the driving body 216, to lock the driving body 216 in a proximal position within the housing 202.

FIG. 7A illustrates a cross-section view of the end effector in a first condition, in accordance with at least one example of the present application. FIG. 7B illustrates a cross-section view of the end effector in a second condition, in accordance with at least one example of the present application. Also shown in FIGS. 7A and 7B are a longitudinal axis A1, and orientation indicators Proximal and Distal. FIGS. 7A and 7B are discussed below concurrently.

FIG. 7A shows that end effector 200 can be in a locked condition. In the locked condition, the driving body 216 can be retained in a superior position within the housing 202, and the first jaw 210 and the second jaw 212 can be open. The first lock spring 277 and the second lock spring 278 can be in a resting state and the drive spring 276 can be in a compressed state. In the resting state, the first lock spring 277 and the second lock spring 278 can still be partially compressed in order to maintain some force to bias the lock 118 to engage the lock recess 266 of the driving body 216. The lock 218 can extend vertically through the transverse opening 238 of the housing 202. The first lock spring 277 and the second lock spring 278 can bias the lock 218 vertically, to allow the inferior ramp 262 of the lock 218 to extend into and engage the driving body recess 266 to lock the driving body 216 in a proximal position; and the first jaw 210 and the second jaw 212 open.

FIG. 7B shows how the end effector 200 can be in an unlocked condition. The lock body 218 can be operated to release the driving body 216 and close the first jaw 210 and the second jaw 212. In some examples, the lock body 218 can be translated substantially orthogonally to the longitudinal axis A1. In the unlocked condition, the first lock spring 277 and the second lock spring 278 can be in a compressed state and the driving spring 276 can be in a resting state.

In operation, the lock 218 can be operated by applying a downward force on the lock 218 to cause the inferior ramp 262 translate downward to disengage the lock recess 266 of the driving body 216 to release the driving body 216. The first lock spring 277 and the second lock spring 278 can be compressed by downward translation of the lock body 218. Once the driving body 216 is released from engagement with the lock 218, the driving spring 276 can drive the driving body 216 distally within the housing 202 to contact the first jaw 210 and the second jaw 212, to cause the first jaw 210 and the second jaw 212 to pivot to close the tool opening 214. The drive spring 276 can be in a resting state once the driving body 216 has translated distally and closed the tool opening 214. In some examples, in the resting state, the drive spring 276 can still be partially compressed in order to maintain some force to hold the driving body 116 in the distal position.

FIG. 7B also shows how the end effector 200 can be operated to close the first jaw 210 and the second jaw 212 by operating the lock release 220 to release the driving body 216 to close the tool opening 214. The lock release 220 can be operated by translating proximally relative to the housing 202, for example, by a surgical tool positioned within the tool opening 214. The first proximal ramp 274 and the second proximal ramp 275 can then engage the first superior ramp 260 and the second superior ramp 261, respectively, of the lock body 218, to cause the lock body 218 to translate downward. When the lock body 218 translates downward, the inferior ramp 262 can disengage from the lock recess 266 of the driving body 216, to release the driving body 216. Once released, the driving body 216 can translate distally within the housing 202 and contact the first jaw 210 and the second jaw 212 to close the tool opening 214. The drive spring 276 can be in resting state once the driving body 216 has translated distally and closed the tool opening 214. In the resting state, the drive spring 276 can still be partially compressed in order to maintain some force to hold the driving body 116 in the distal position.

When it is desired to re-open the first jaw 210 and the second jaw 212, the end effector 200 can be returned to the locked condition through proximal translation of the first 222 and second projection 226, and the transverse body 224, such as by using the projections 222 and 226 to translate the driving body 216 proximally to overcome the force of the driving spring 276, until the inferior ramp 262 of lock body 218 is aligned with the lock recess 266. When the driving body 216 is translated to the proximal position, the first lock spring 277 and the second lock spring 278 can drive the lock body 218 vertically to engage the lock 218 with the driving member 216. Such a process can be repeated, as desired.

The ability of the lock 218 to be operated to close the tool opening 214 by both direct operation, and by indirect operation through the lock release 220, can provide a user with two separate methods to retain a surgical tool within the tool opening 214 without the use of a second hand. This ability can be advantageous during surgical operations where a surgeon may not be able to use two hands or may not be able to manually operate the lock 218, while simultaneously holding a surgical tool in the tool opening 214. This ability can also save time during a surgical procedure.

FIG. 8 illustrates a method for using an end effector, in accordance with at least one example of the present application. The steps or operations of the method 300 are illustrated in a particular order for convenience and clarity; many of the discussed operations can be performed in a different sequence or in parallel without materially impacting other operations. The method 300 as discussed includes operations that can be performed by multiple different actors, devices, and/or systems. It is understood that subsets of the operations discussed in the method 300 can be attributable to a single actor, device, or system and could be considered a separate standalone process or method. In this example, the method 300 includes operations such as engaging the drive spring at 302, moving the lock body at 304, opening the jaws at 306, positioning a surgical tool at 308, and closing the jaws at 310.

In one or more examples, the method 300 can begin at step 302 with a user engaging a proximal portion of a housing and a driving body, with a drive spring, to bias the driving body distally. For example, as shown in FIGS. 3A-3D, engaging the proximal portion 110 of the housing 108 and the driving body 124 can include engaging the drive spring 186 to bias the driving body 124 distally. In one or more examples, a second step 304 can include moving a lock body to an unlocked position to disengage the housing. In one or more examples, the second step can include positioning a tool between the opposing jaws. For example, as shown in FIGS. 4A-4C, the lock 126 can be pivoted to contact the lock projection 127 and translate the lock body 174 into the lock cavity 175, so that the lock body 174 is disengaged from the transverse slot 144 of the housing 108, releasing the driving body 124 from the housing 108.

In one or more examples, a third step 306 can include translating the driving body within the housing along a longitudinal axis of the housing to open opposing jaws pivotably coupled to the housing. For example, as shown in FIG. 3A-3B the end effector 100 can be returned to the locked condition through proximal translation of the driving body 124, such as by using the projections 187 to translate the driving body 124 proximally, until the lock body 174 is aligned with the transverse slot 144; allowing the lock spring 188 to drive the lock body 174 vertically to enter the transverse slot 144, and engage the housing 108 to limit translation of the lock 126 with respect to the housing 108. Such a process can be repeated, as desired.

In one or more examples, a user can engage a proximal portion 110 of the housing 108 with a drive spring 186 (302). The user can move the lock 126 to an unlocked position to disengage the housing (304). The user can translate the driving body 124 proximally within housing 108 to open the first 118 and the second 120 jaws (306). The user can position a surgical tool between the first 118 and the second 120 jaws (308). The user can translate the driving body 124 distally within housing 102 to close the first 118 and the second 120 jaws (310). Such a method can be repeated, as desired.

NOTES AND EXAMPLES

The following, non-limiting examples, detail certain aspects of the present subject matter to solve the challenges and provide the benefits discussed herein, among others.

Example 1 is an end effector for a surgical arm comprising: a housing extending along a longitudinal axis, the housing comprising a proximal portion and a distal portion; a stem secured to the proximal portion of the housing, the stem configured to releasably couple the end effector to the surgical arm; a pair of opposing jaws pivotably coupled to the housing, and extending outwardly from the distal portion of the housing to form a tool opening; a driving body translatable within the housing along the longitudinal axis, the driving body operable to open the opposing jaws and expand the tool opening when the driving body translates proximally and to close the opposing jaws and contract the tool opening when the driving body translates distally; a drive spring positioned within the housing to engage the proximal portion of the housing and the driving body to bias the driving body distally; and a lock body extending through the housing, the lock body movable between a locked position and an unlocked position, the lock body configured to engage the housing and the driving body in the locked position to limit distal translation of the driving body with respect to the housing.

In Example 2, the subject matter of Example 1 optionally includes wherein the proximal portion of the housing includes a threaded member, the threaded member extending proximally along the longitudinal axis.

In Example 3, the subject matter of Example 2 optionally includes a threaded collar coupled to the threaded member of the housing, the threaded collar threadable distally along the threaded member to engage and distally translate the driving body and to limit proximal translation of the driving body.

In Example 4, the subject matter of Example 3 optionally includes wherein the threaded member of the driving body includes a friction element configured to engage the threaded collar and retain the threaded collar in a position.

In Example 5, the subject matter of any one or more of Examples 1-4 optionally include a lock pivotably coupled to the housing and operable to engage the lock body to disengage the lock body from the housing to allow the driving body to translate distally to close the pair of jaws and the tool opening.

In Example 6, the subject matter of Example 5 optionally includes wherein engagement of the lock with the lock body causes the lock to translate substantially orthogonally to the longitudinal axis to disengage the housing.

In Example 7, the subject matter of any one or more of Examples 5-6 optionally include wherein the lock includes a lock projection movable through the housing to engage the lock body when the lock is operated to close the pair of jaws and the tool opening.

Example 8 is the end effector of Example 1, further comprising a lock release coupled to the distal portion of the housing, the lock release operable to engage the lock to release the driving body and close the tool opening.

In Example 9, the subject matter of Example 8 optionally includes wherein the lock release is positioned within the tool opening between the opposing jaws and is configured to be engaged by a tool positioned within the tool opening to close the pair of jaws around the tool to secure the tool within the tool opening.

In Example 10, the subject matter of any one or more of Examples 8-9 optionally include wherein the lock release includes a proximal ramp and the lock includes a rounded distal surface, the proximal ramp engageable with the rounded distal surface when the lock release is translated distally to move the lock upward and pivot about the housing to move the lock body out of the locked position.

In Example 11, the subject matter of any one or more of Examples 8-10 optionally include wherein the lock release includes an oblong bore configured to receive a pin therethrough to guide translation of the lock release with respect to the housing.

In Example 12, the subject matter of any one or more of Examples 1-11 optionally include wherein the opposing jaws are pivotably coupled within the distal portion of the housing by a pin extending through the opposing jaws and connected to the housing.

In Example 13, the subject matter of any one or more of Examples 1-12 optionally include wherein the lock body engages with a transverse slot formed in the proximal portion of the housing to limit distal translation of the driving body when the lock body is in the locked position.

In Example 14, the subject matter of any one or more of Examples 1-13 optionally include a lock spring engageable with the lock body and the driving body to bias the lock body to the locked position such that the lock body engages the housing.

In Example 15, the subject matter of any one or more of Examples 1-14 optionally include wherein the driving body extends outward of the housing and is operable to proximally translate along the longitudinal axis to open the pair of jaws and the tool opening.

In Example 16, the subject matter of any one or more of Examples 1-15 optionally include a projection coupled to the driving body outside the housing, the projection operable to translate the driving body proximally.

In Example 17, the subject matter of any one or more of Examples 1-16 optionally include wherein the driving body includes two openings, each opening configured to receive a proximal end of one of the opposing jaws.

In Example 18, the subject matter of Example 17 optionally includes wherein the driving body includes a guide protrusion aligned with the longitudinal axis and separating the two openings, the guide protrusion configured to contact each of the opposing jaws when the driving body is translated proximally to guide the jaws into their respective openings to open the jaws.

In Example 19, the subject matter of Example 18 optionally includes wherein the drive member includes a first arm and a second arm extending substantially orthogonally to the longitudinal axis, the first arm and the second arm configured to contact the opposing jaws to close the tool opening when the driving body is translated distally.

Example 20 is an end effector for a surgical arm comprising: a housing extending along a longitudinal axis, the housing comprising a proximal portion and a distal portion; a pair of opposing jaws pivotably coupled to the housing, and extending outwardly from the distal portion of the housing; a driving body translatable within the housing along the longitudinal axis, the driving body translatable within the housing to open and close the opposing jaws; a drive spring positioned within the housing to engage the proximal portion of the housing and the driving body to bias the driving body distally; and a lock body extending through the housing, the lock body movable between a locked and an unlocked position, the lock body configured to engage the housing and the driving body in the locked position to limit distal translation of the driving body with respect to the housing.

In Example 21, the subject matter of any one or more of Examples 1-20 optionally include a stem secured to the proximal portion of the housing, the stem configured to releasably couple the end effector to the surgical arm.

In Example 22, the subject matter of any one or more of Examples 1-21 optionally include wherein the driving body opens the opposing jaws and the tool opening when the driving body translates proximally and closes the opposing jaws and the tool opening when the driving body translates distally.

Example 23 is a method of using an end effector, the method comprising: engaging a proximal portion of a housing and a driving body, with a drive spring, to bias the driving body distally; moving a lock body to an unlocked position to disengage the housing; and translating the driving body within the housing along a longitudinal axis of the housing to open opposing jaws pivotably coupled to the housing.

In Example 24, the subject matter of Example 23 optionally includes wherein moving the lock body to unlocked position to disengage the housing; and translating the driving body within the housing along a longitudinal axis of the housing to open opposing jaws pivotably coupled to the housing.

In Example 24, the subject matter of Example 23 optionally includes wherein moving the lock body to an unlocked position to disengage the housing comprises positioning a tool between the opposing jaws.

What is claimed is:

1. An end effector for a surgical arm comprising:
a housing extending along a longitudinal axis, the housing comprising a proximal portion and a distal portion;

a stem secured to the proximal portion of the housing, the stem configured to releasably couple the end effector to the surgical arm;

opposing jaws pivotably coupled to the housing, and extending outwardly from the distal portion of the housing to form a tool opening;

a driving body translatable within the housing along the longitudinal axis, the driving body operable to open the opposing jaws and expand the tool opening when the driving body translates proximally and to close the opposing jaws and contract the tool opening when the driving body translates distally;

a drive spring positioned within the housing to engage the proximal portion of the housing and the driving body to bias the driving body distally; and a lock body extending through the housing, the lock body movable between a locked position and an unlocked position, the lock body configured to engage the housing and the driving body in the locked position to limit distal translation of the driving body with respect to the housing.

2. The end effector of claim 1, wherein the proximal portion of the housing includes a threaded member, the threaded member extending proximally along the longitudinal axis.

3. The end effector of claim 2, further comprising a threaded collar coupled to the threaded member of the housing, the threaded collar threadable distally along the threaded member to engage and distally translate the driving body and to limit proximal translation of the driving body.

4. The end effector of claim 3, wherein the threaded member of the driving body includes a friction element configured to engage the threaded collar and retain the threaded collar in a position.

5. The end effector of claim 1, further comprising:

a lock pivotably coupled to the housing and operable to engage the lock body to disengage the lock body from the housing to allow the driving body to translate distally to close the opposing jaws and the tool opening.

6. The end effector of claim 5, wherein engagement of the lock with the lock body causes the lock to translate substantially orthogonally to the longitudinal axis to disengage the housing.

7. The end effector of claim 5, wherein the lock includes a lock projection movable through the housing to engage the lock body when the lock is operated to close the opposing jaws and the tool opening.

8. The end effector of claim 5, further comprising a lock release coupled to the distal portion of the housing, the lock release operable to engage the lock to release the driving body and close the tool opening.

9. The end effector of claim 8, wherein the lock release is positioned within the tool opening between the opposing jaws and is configured to be engaged by a tool positioned within the tool opening to close the opposing jaws around the tool to secure the tool within the tool opening.

10. The end effector of claim 8, wherein the lock release includes a proximal ramp and the lock includes a rounded distal surface, the proximal ramp engageable with the rounded distal surface when the lock release is translated distally to move the lock upward and pivot about the housing to move the lock body out of the locked position.

11. The end effector of claim 8, wherein the lock release includes an oblong bore configured to receive a pin therethrough to guide translation of the lock release with respect to the housing.

12. The end effector of claim 1, wherein the opposing jaws are pivotably coupled within the distal portion of the housing by a pin extending through the opposing jaws and connected to the housing.

13. The end effector of claim 1, wherein the lock body engages with a transverse slot formed in the proximal portion of the housing to limit distal translation of the driving body when the lock body is in the locked position.

14. The end effector of claim 1, further comprising a lock spring engageable with the lock body and the driving body to bias the lock body to the locked position such that the lock body engages the housing.

15. The end effector of claim 1, wherein the driving body extends outward of the housing and is operable to proximally translate along the longitudinal axis to open the opposing jaws and the tool opening.

16. The end effector of claim 1, further comprising a projection coupled to the driving body outside the housing, the projection operable to translate the driving body proximally.

17. The end effector of claim 1, wherein the driving body includes two openings, each opening configured to receive a proximal end of one of the opposing jaws.

18. The end effector of claim 17, wherein the driving body includes a guide protrusion aligned with the longitudinal axis and separating the two openings, the guide protrusion configured to contact each of the opposing jaws when the driving body is translated proximally to guide the jaws into their respective openings to open the jaws.

19. The end effector of claim 18, wherein the driving body includes a first arm and a second arm extending substantially orthogonally to the longitudinal axis, the first arm and the second arm configured to contact the opposing jaws to close the tool opening when the driving body is translated distally.

20. An end effector for a surgical arm comprising:

a housing extending along a longitudinal axis, the housing comprising a proximal portion and a distal portion;

opposing jaws pivotably coupled to the housing, and extending outwardly from the distal portion of the housing to form a tool opening;

a driving body translatable within the housing along the longitudinal axis, the driving body translatable within the housing to open and close the opposing jaws;

a drive spring positioned within the housing to engage the proximal portion of the housing and the driving body to bias the driving body distally; and a lock body extending through the housing, the lock body movable between a locked position and an unlocked position, the lock body configured to engage the housing and the driving body in the locked position to limit distal translation of the driving body with respect to the housing.

21. The end effector of claim 20, further comprising a stem secured to the proximal portion of the housing, the stem configured to releasably couple the end effector to the surgical arm.

22. The end effector of claim 20, wherein the driving body opens the opposing jaws and the tool opening when the driving body translates proximally and closes the opposing jaws and the tool opening when the driving body translates distally.

* * * * *